United States Patent [19]

Voronkov et al.

[11] 4,055,637

[45] Oct. 25, 1977

[54] MEDICINAL PREPARATION FOR HEALING WOUNDS AND TREATING DERMATITES USING 1-(CHLOROMETHYL)SILATRANE

[76] Inventors: Mikhail Grigorievich Voronkov, ulitsa Lermontova, 315, kv.32; Ada Timofeevna Platonova, ulitsa Lermontova, 313, kv.31; Ljudmila Andreevna Mansurova, ulitsa Lermontova, 333, kv.153; Igor Georgievich Kuznetsov, ulitsa Lermontova, 325, kv.36, all of Irkutsk; Gunar Izidorovich Zelchan, ulitsa Moskovskaya, 256/4, kv.11, Riga; Valery Mikhailovich Dyakov, ulitsa Lermontova, 263, kv.23, Irkutsk, all of U.S.S.R.

[21] Appl. No.: 605,202

[22] Filed: Aug. 15, 1975

[51] Int. Cl.$^2$ .......................................... A61K 31/695
[52] U.S. Cl. .................................................. 424/184
[58] Field of Search ................. 424/184; 260/448.8 R

[56] References Cited

U.S. PATENT DOCUMENTS 3,133,108  5/1964  Finestone ........................ 260/448.2

OTHER PUBLICATIONS

Chem. Abst., vol. 79, (1973), 5384u, Voronkoy et al..
The Merck Index of Chem. & Drugs, (1960), pp. 596, 775 & 788.

*Primary Examiner*—Allen J. Robinson
*Attorney, Agent, or Firm*—Haseltine, Lake & Waters

[57] ABSTRACT

A medicinal preparation for healing wounds and treating dermatites which comprises an active principle, viz. 1-chloromethylsilatrane of the following formula:

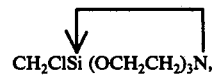

combined with a pharmaceutical carrier.

2 Claims, No Drawings

MEDICINAL PREPARATION FOR HEALING WOUNDS AND TREATING DERMATITES USING 1-(CHLOROMETHYL)SILATRANE

The present invention relates to a novel medicinal preparation for healing wounds and treating dermatites.

In accordance with the invention, the proposed medicinal preparation for healing wounds and treating dermatites comprises an active principle, viz. 1-(chloromethyl)silatrane of the following formula:

$$CH_2ClSi(OCH_2CH_2)_3N,$$

combined with a pharmaceutical carrier.

The active principle of the proposed medicinal preparation, 1-(chloromethyl)silatrane, is a white crystalline powder poorly soluble in water, readily soluble in chloroform, difficultly soluble in alcohol and insoluble in ether, having a melting point anywhere from 215° to 222° C. within 2°, melting without decomposition, non-hygroscopic, and sterilizable in a dry state.

The proposed preparation exhibits a wound-healing effect and is a potent means of treating dermatites. It finds application in the treatment of fresh wounds, persistent ulcers and dermatites of various etiology, including allergic dermatites.

The mechanism of the proposed preparation consists in improving the exchange of silicon, a minor element essential to the formation of connective tissue. It boosts the growth of fibrous structures, raises the temperature at the site of application and has a local stimulating effect on metabolic processes.

The effect of the medicinal preparation of this invention was studied for different modes of application and for a variety of doses. For the sake of comparison, similar studies were performed on Višnevski's ointment, synthomycin emulsion and Zigerol (a cheese albumin preparation). The study involved 110 rabbits on which dermatomuscular wounds from 300 to 600 sq.mm. in area were inflicted (the latter in the 4th and 5th series). The first series included three groups of animals (two experimental groups each comprising 5 animals and a control one comprising 3 rabbits). The preparation was administered subcutaneously in an aqueous solution at the rate of 50 mg per 1 kg of body weight. The preparation was administered daily from the day the wound was inflicted to the day of complete healing. The healing periods were as follows: 22 days in the controls and 16 days in the experimental groups.

The second series of experiments was conducted on 23 animals: three experimental groups each comprising 6 rabbits and a control group including 5 animals. The preparation was administered subcutaneously at a dose of 50 mg/kg and was also applied to the wound as a 5-percent ointment prepared on a Vaseline-lanolin base.

The healing periods were as follows: 20 days in the control group; 16 days in the subcutaneous-administration group; and 10 days in the cutaneous-application group.

In the third series of experiments, the proposed preparation was compared with Višnevski's ointment and the synthomycin emulsion.

The healing periods were as follows: Višnevski's ointment, 18 days; synthomycin emulsion, 17 days; the proposed preparation, 11 days.

The fourth and fifth series were characterized by certain apecific features. The experiment involved large rabbits. The study was carried out in summer when the animals' diet included a large proportion of green fodder. The wounds inflicted on the rabbits were twice the size of the wounds in the preceding series. The preparations were made in the form of 5-percent ointments. The experiment involved two groups of rabbits, 5 animals per group. The ointments were applied onto the wounds daily. Th controls were subjected to no treatment. The healing periods were as follows: controls, 22 days; Zygerol, 16 days; the proposed preparation, 10 days.

The proposed preparation was proved to have no toxic properties.

Administered intraperitoneally, the preparation's $LD_{50}$ is 3,000 mg/kg.

The preparation of this invention was clinically tested on 120 patients with fresh wounds, suppurative wounds, surface burns, and dermatites of various etiology, including allergic dermatites.

Used to treat small abrasions, irritations, skin burns and erosion, the proposed preparation took almost half again as little or half the time to effect a cure as compared with the other drugs. Small wounds healed under a crust with a soft and tender scar. The proposed preparation entailed no complications.

In clinical use, the preparation was applied directly onto the wound surface or a onto sterile dressing. The dressings were changed daily or every other day until the wounds healed completely.

The trials were carried out by administering local treatment to patients with fresh surface burns (2nd or 3rd degree) within the first 1 to 3 days after the trauma. The preparation caused an adequate rate of epithelization unencumbered by the insignificant purulent-serous discharge observed. In this group of patients, the wounds took 10 to 15 days to heal.

The preparation of this invention was likewise found an effective means of treating persistent wounds of donor sites due to the suppuration of some spots after skin flaps had been cut off with a dermatome. In these patients, too, the wounds healed fairly quickly.

Applied to treat postoperative wounds stitched with a silk thread, the preparation of this invention effected a cure within the usual period (from 7 to 10 days) before suture removal.

In order to determine the efficacy of the proposed preparation and to study its effect on the patients, apart from clinical observation, the patients were studied for hemoglobin and red-cell count, blood colour index, white-cell count or differential blood-count, sedimentation rate, total protein, residual nitrogen and bilirubin of the blood, as well as the specific weights and microscopic characteristics of the morphological constituents of the urine. All deviations of some of the above characteristics from normal values usually occurred postoperatively or in the degenerative-inflammatory period of the wound-healing process and returned to normal in the regenerative period.

In accordance with the invention, the proposed medicinal preparation comprises an active principle, 1-(chloromethyl)silatrane, combined with a pharmaceutical carrier. The pharmaceutical carrier is preferably an ointment base, viz. lanolin with Vaseline, or a vegetable oil such as peach kernel oil or linseed oil.

The level of the active principle in the ointments ranges from 1 to 5 percent by weight.

Various nutrient creams may likewise serve as the base for the preparation ointments, but then the ointment is prepared ex tempore for the preparation is decomposed by water during storage.

The preparation ointment is applied in a thin layer either directly onto the wound or onto a gauze cloth which is applied to the wound daily or every other day.

The preparation has no irritating effect, is easily tolerated by the patients and produces no side effects.

The active principle of the proposed preparation, viz. 1-chloromethylsilatrane, is preferably prepared as follows.

Triethanolamine is admixed with absolute ethanol and KOH. The solution is heated to boiling and (chloromethyl)trimethoxysilane is added thereto. The white crystalline precipitate formed thereby is drawn off by suction and dried in a vacuum.

The white powder thus obtained is recrystallized from chloroform to produce a pure desired product, viz. 1-(chloromethyl)silatrane, having a melting point of 220° to 221° C. The yield of the end product is up to 90 percent by weight.

What is claimed is:

1. A method for healing wounds in patients which comprises topically administering to a patient in need of such treatment a wound-healing effective amount of a medicinal composition containing from 1 to 5% by weight of 1-(chloromethyl)silatrane of the formula

in a pharmaceutical carrier selected from the group consisting of lanolin-petroleum jelly and vegetable oil.

2. The method as set forth in claim 1, wherein the vegetable oil is selected from the group consisting of peach kernel oil and linseed oil.

* * * * *